United States Patent [19]

Eger et al.

[11] 4,242,832

[45] Jan. 6, 1981

[54] PROCESS FOR PREPARING MONOKARYONS BY DEDIKARYOTIZING DIKARYOTIC STRAINS OF BASIDIOMYCETES

[76] Inventors: Gerlind Eger, Leckergässchen 2, 3550 Marburg an der Lahn; Hermilo Leal Lara, Richtsberg 88-602, Marburg an der Lahn, both of Fed. Rep. of Germany

[21] Appl. No.: 23,772

[22] Filed: Mar. 26, 1979

[30] Foreign Application Priority Data

Mar. 29, 1978 [DE]   Fed. Rep. of Germany ....... 2813521

[51] Int. Cl.³ .............................................. A01G 1/04
[52] U.S. Cl. ....................................... 47/1.1; 435/254
[58] Field of Search .................... 47/1.1; 435/254, 101

[56] References Cited

U.S. PATENT DOCUMENTS

4,159,225   6/1979   Yoshikumi et al. .................. 435/101

OTHER PUBLICATIONS

The Biology and Cultivation of Edible Mushrooms, Chang et al., 1978, Academic Press.

*Primary Examiner*—Robert E. Bagwill
*Attorney, Agent, or Firm*—Kenyon & Kenyon

[57] ABSTRACT

The invention relates to a process for producing monokaryons of dikaryotic strains of Basidiomycetes by chemical means, for instance *Pleurotus ostreatus, Kuehneromyces mutabilis, Flammulina velutipes* or *Lentinus edodes* under gentle conditions so that essentially two monokaryons result per dikaryon-containing hyphal compartment. These monokaryons can be used for mating with compatible partners to give dikaryotic Basidiomycetes strains.

15 Claims, No Drawings

PROCESS FOR PREPARING MONOKARYONS BY DEDIKARYOTIZING DIKARYOTIC STRAINS OF BASIDIOMYCETES

The dikaryotic Basidiomycetes include some of the most important edible mushrooms which are produced in large quantities on agricultural waste products. The methods so far used to breed such strains for producing edible mushrooms essentially consist in selecting naturally occurring dikaryons (which contain two different nuclei per hyphal compartment) in isolating monokaryons (which contain one nucleus per hyphal compartment) via individual spores of fruit bodies of these dikaryons, and in combining monokaryons to form new dikaryons which are selected in accordance with the properties desired. When undergoing meiosis during spore formation the genes of a dikaryon are randomly distributed onto the spores. In this process, new advantageous gene combinations can appear, however, especially good gene combinations may also be lost. This method of breeding is not feasible for breeding dikaryons with sporeless fruit bodies—in the following called "sporeless strains"—since there are no spores.

Sporeless strains are, however, highly desirable for the following reasons.

Spores of edible mushrooms are allergens for humans and animals (T. KONDO et al., Japan J. Allergy, vol. 18, (1969), p. 81; K. SHICHIJO et al., Japan. J. Clin. Med., vol. 28, (1970), p. 575; F. ZADRAZIL, Naturwissenschaften, vol. 61, (1974), p. 456; U. NOSTER et al., Deutsche Med. Wochenschr., vol. 101, (1976), p. 1241-1245). Moreover, the uncontrollable spore propagation of species which decompose wood can attack woods of any kind and can thus cause considerable damage. Finally, virus can be transmitted by spores from one culture to another (A. DIELEMAN-VAN ZAAYEN, Mushroom Science VIII, London, 1972, p. 131-154; Der Champignon No. 183, November 1976) and can endanger mushroom cultivation itself.

Sporelessness appears as spontaneous mutation or after treatment with mutagens (T. TAKEMARU and T. KAMADA, Report Tottori Mycol. Inst. Japan, vol. 9 (1971), p. 21-35). Therefore, sporeless strains are frequently multiple mutants which, apart from the desired sporelessness, also possess undesired properties, such as too slow growth, low fruit body yield, and abnormal fruit bodies. T. TAKEMARU and T. KAMADA (Report Tottori Mycol. Inst. Japan, vol. 9, (1971), p. 21-35) and G. EGER et al. (Theoretical and Applied Genetics, vol. 47 (1976), p. 155-163) tried to combine the sporelessness in a dikaryon by pairing it with a monokaryon to obtain a new dikaryon. This method is problematic (G. EGER et al., Theoretical and Applied Genetics, vol. 47, (1976), p. 155-163) and does not allow intentional breeding. The latter requires knowledge of the genes present in the breeding material. It further requires the knowledge of the distribution of these genes onto the individual nuclei and this intentional combination to new strains. The genetics of sporelessness is as yet unknown.

In the past, repeated attempts have been made to dedikaryotize dikaryotic strains. The surgical method by R. HARDER (Z. für Botanik, vol. 19 (1927), p. 337-407) was also applied by N. FRIES and K. ASCHAN (Svenks Bot. Tidskr., vol. 46 (1952), p. 365 to 391 and p. 429 to 445). It is disadvantageous in that it is very troublesome and can be carried out only by highly qualified personnel and in that predominantly one type of monokaryons is obtained instead of the two expected.

G. MILES and J. R. RAPER (Mycologia, vol. 48 (1956), p. 484-494) have therefore attempted a chemical dedikaryotization using bile acids and sodium taurocholate respectively. T. TAKEMARU (Report Tottori Mycol. Inst. Japan, vol. 4 (1964), p. 37-40 and 41-43) used ox-gall and sodium cholate. In both cases, with 50 to 120 isolates, respectively, it was generally only possible to isolate one of the two component nuclei of a dikaryon. These also included mutants. Y. PARAG (Can. J. Microbiol, vol. 7 (1961), p. 838-841), R. M. KERRUISH and E. W. B. DACOSTA (An. Botany, vol. 27 (1963), p. 653-670), T. L. AMBURGEY (Phytopathology, vol. 57 (1967), p. 486-491), M. McCLAREN (Can. J. Botany, vol. 48 (1970), p. 787-790), T. TAKEMARU and T. KAMADA (Report Tottori Mycol. Inst. Japan, vol. 9 (1971), p. 21-35) treated dikaryons with different cell toxins. In some cases they succeeded in isolating monokaryons. In each case they obtained only one nucleus type, namely that nucleus type of the initial dikaryon which is more resistant to the cell toxin used. The yield in monokaryons was very low and mutants appeared. A. GINTEROVA (Folia Microbiol., vol. 18 (1973), p. 277-280) finally observed dedikaryotization, if a dikaryon was agitated with a specific frequency in a liquid. The dedikaryotization occurred also in this case at the expense of one nucleus of the initial dikaryon.

The problem underlying the invention is to provide a novel method for dedikaryotizing dikaryotic strains of Basidiomycetes mycetes so that both nuclei of a given dikaryon can be isolated in high yields and in a reproducible manner at any time without changing the genes.

This problem is solved by the process steps described in the claims. With the monokaryons produced according to the invention and compatible partners it is possible to produce dikaryotic strains of Basidiomycetes, so-called dikaryons, which contain two different nuclei per hyphal compartment (cell).

The solution of the inventive problem resides in the development of a new dedikaryotization process. With this process the two nuclei of a dikaryon can be separated from each other so gently that two types of monokaryons result. The two types of monokaryons, also called neohaplonts contain each one unchanged nucleus type of the initial dikaryon. With the inventive process it is possible to determine which genes that are important for breeding are located in the individual monokaryons. It allows the selection of the monokaryons with the set of genes desired in the particular case and then combination with new monokaryotic partners to form dikaryons with improved properties. Furthermore, it makes it possible to identify dikaryons and thus to prove unauthorized propagation. Finally, it also makes it possible to prove unauthorized removal of a nucleus from a dikaryon and its mating with another monokaryon.

The inventive process has the following advantages over the known methods:

1. The process does not require expensive equipment or great expenditure for staff (like the surgical method) and can therefore be carried out in any microbiological laboratory.
2. The proccess is much faster than any of the methods hitherto known.

3. The process consistently gives two monokaryon types in high yield with the result that the expenditure for their isolation is low.
4. The nuclei of the monokaryons are identical with the nuclei of the initial material, thanks to the gentle treatment.
5. The dedikaryotization of a given dikaryon gives reproducible results even if repeated at prolonged intervals.
6. Even monokaryons with abnormal morphology or metabolic blockades (auxotrophic mutants), which were introduced into a dikaryon in order to mark a strain, can be recovered from this dikaryon as monokaryons.
7. The process makes it possible for the first time to breed sporeless strains on a controlled and regular basis so that they endanger neither men nor the environment.
8. The process makes it possible for the first time to identify a dikaryotic edible mushroom strain in a simple manner.
9. The process makes it possible for the first time to prove unauthorized propagation of a dikaryotic mushroom strain.
10. Furthermore, the process makes it possible for the first time to prove unauthorized removal of a nucleus from a specified dikaryon for the purpose of breeding.

The individual steps of the inventive process are specified below.

(A) Dedikaryotization of the initial material
(B) Identification of the mating compatibility of monokaryons
(C) Identification of important genes, for instance of the genes for sporelessness, in monokaryons
(D) Identification of characteristic features of monokaryons and of dikaryons formed therefrom
(E) Mating of selected monokaryons with new partners to form new dikaryons
(F) Examination of the new dikaryons as to the stability of their characteristics by repeated dedikaryotization
(G) Definition of the strains.

(A) Dedikaryotization of the initial material

As initial material a dikaryotic Basidiomycete is used, preferably oyster-mushroom (*Pleurotus ostreatus*), winter mushroom (*Flammulina velutipes*), *Kuehneromyces mutabilis* and Shiitake (*Lentinus edodes*). It can be a wild strain or a strain treated with a mutagene. The essential point is that it possesses properties that are valuable from the aspect of breeding, such as sporelessness. Each mushroom strain is cultured under conditions suitable for its growth if possible under optimal conditions.

The vegetative form of the fungus, the so-called mycelium, is fragmented in sterilized containers of a mixer or mincing apparatus (for instance "Waring Blendor") with rotating knives while liquid is added (sterile, distilled water, tap water, physiological sodium chloride solution, buffer or dedikaryotizing solution) in such a way that at least about 50% of the viable mycelial fragments have one hyphal compartment and the remaining fragments no more than about 2–4 hyphal compartments. The temperature must be controlled by cooling so that it at no time increases to or exceeds the maximum temperature of the respective fungus. If unknown, the maximum temperature of the respective fungus is easy to determine. A small amount of the fragments is inoculated into the lower part of the dedikaryotizing solution. Care must be taken to ensure that the fragments and the mycelial pellets developing therefrom are are always covered by at least 2 mm by a liquid layer. The number of the fragments should be small enough to allow the fragments to grow fully on the bottom of the liquid to form isolated mycelial pellets. The preparations in the dedikaryotizing solution are incubated at a temperatures of 2° to 35° C., most preferably at the temperature which is optimal for the growth of the respective fungus strain.

The dedikaryotizing solution used is a sterilized, preferably heat-sterilized liquid containing at least one carbon source (e.g., glucos, miultos) and a neutral peptone obtained from meat with the aid of pepsin, which peptone is characterized by a high glycine content (at least about 10% of total amino acids) and low phosphate (as $P_2O_5$ determined less than about 7%) and magnesium (less than about 100 p.p.m.) content, such as "Peptone P" (by OXOID L 49), or a mixed peptone which contains this peptone or another one of similar quality and composition or glycine instead of the peptone, or any other liquid with corresponding glycine content. The neutral meat peptone is used in an amount of 0.02 to 7% and the glycine in an amount of 0.01 to 5%. If the dikaryon to be dedikaryotized or one of its monokaryotic components is auxotrophic with respect to the growth factors or nitrogen-containing compounds, the dedikaryotizing solution must be supplemented with small amounts of corresponding compounds.

After the mycelial fragments have grown in the dedikaryotizing solution into visible mycelial pellets, random samples are microscopically examined at low magnification (up to 100 times) for their degree of dedikaryotization. If conditions are optimal, the yield in monokaryons is 100%. The mycelial pellets are again fragmented into fragments having one or a very few cells, under the same conditions as in step (a) of the claims 1 and 2.

The fragments are then placed on or in nutrient agar plates after diluting the fragments so that they can grow into spatially isolated individual colonies. The basis for the nutrient agar is a nutrient medium which is suitable for the respective fungus. The plates are incubated, preferably at the temperature which is optimal for the respective fungus, until the colonies can be perceived with the naked eye. If necessary (dedikaryotization degree of the mycelial pellets smaller than 100%), the individual colonies are examined at low magnification as to their monokaryotic state. It is frequently possible to recognize two types of colonies macroscopically. An inoculum from each of not more than 5 colonies of each type (not more than 10 in all) is transferred to a new nutrient medium. If all colonies look alike, the inoculation material will be taken from not more than 20 colonies in all.

(B) Identification of the mating compatibility of monokaryons

The sexuality and thus also the fertility of Basidiomycetes is controlled by A and B factors (mating factors). The species mentioned herein of the genera Pleurotus, Flammulina, Kuehneromyces and Lentinus possess two A and two B factors. In nature there exist numerous alleles for either one. For *Pleurotus ostreatus* at least 63 A and 190 B factors have been estimated (C. P. EUGENIO and N. A. ANDERSON, Mycologia, vol. 60 (1968), p. 627–634). A monokaryon developed from a single sexual spore contains one A and one B factor.

Two monokaryons can combine to form a dikaryon if the A and B factors are different, for instance $A_{23}B_{14}$ and $A_{35}B_{54}$. The dikaryon forms fruit bodies with basidia in which the two nuclei fuse and undergo meiosis. Finally four daughter nuclei are formed which migrate into spores. Among the spores of a fruit body there are four types which occur with the same frequency as regards the mating factors. In each case two types correspond to the mating factors of the initial monokaryon, for instance $A_{23}B_{14}$ and $A_{35}B_{54}$, while the other two are recombinants, for instance $A_{23}B_{54}$ and $A_{35}B_{14}$.

In the majority of cases, the dikaryon is characterized by a special morphology, it has so-called clamp connections (in German 'Schnallen'). If the A and B factors in the two mycelia are the same or only the A factor or B factor is the same, then no dikaryon is formed. In the case of identical A factors, nuclei migrate from one mycelium into the other, a fact which can easily be detected by further matings; see K. ESSER, "Kryptogamen", Springerverlag, Berlin-Heidelberg-New York 1976, p. 452–455 and p. 479–496. Consequently, the respective mating factors of a monokaryon can be conclusively identified by mating the monokaryon with test strains (testers) for mating factors. For instance, the monokaryons obtained in step (A) from specific dikaryons treated with a mutagene are brought into contact with four testers corresponding to the respective spore types of the initial dikaryon; see table I. Of the testers in the table, tester 1 and tester 2 are compatible as are tester 3 and tester 4.

Table I

The mating factors (MF) of the monokaryons (Nh) of a strain, which were obtained in step (A) are identified by mating with four testers of the initial dikaryon

| | Tester 1 ($A_1B_1$) | Tester 2 ($A_2B_2$) | Tester 3 ($A_1B_2$) | Tester 4 ($A_2B_1$) | MF of the Nh |
|---|---|---|---|---|---|
| Nh 1 | − | + | − | − | $A_1B_1$ |
| Nh 2 | + | − | − | − | $A_2B_2$ |

Note: Plus = dikaryon formation; minus = no dikaryon formation (C) Identification of important genes, for instance of the genes for sporelessness, in monokaryons Genes for sporelessness can be present in monokaryons obtained from individual spores as well as in monokaryons obtained from dedikaryotized dikaryons. They can be recognized by mating with test monokaryons (testers) for sporelessness. Mating of such testers with monokaryons containing a gene for sporelessness results in sporeless dikaryons. The individual dikaryons originating from such matings are propagated and cultivated in petri dishes. They are made to form fruit bodies in the laboratory according to a rapid method (G. EGER in Mushroom Science, vol. IX/1 (1974), p. 567–573, and Theoretical and Applied Genetics, vol. 47 (1976), p. 155. The gills of the fruit bodies are examined at low microscopic magnification (up to 100 times) for spores. An example is given in table II below.

Table II

The genes for sporelessness (Sp-) are identified by mating monokaryons (Nh) of a strain, which were obtained in step (A), with testers for sporelessness, and the dikaryons are subsequently examined for sporeless fruit bodies.

| | Tester for Sporelessness 1 ($A_2B_2$) | 2 ($A_1B_1$) | Classification of the Nh |
|---|---|---|---|
| Nh 1 | sporeless | no dikaryon | gene for Sp- |
| Nh 2 | no dikaryon | great number of spores | — |

Accordingly, monokaryon 1 has a gene for sporelessness.

(D) Identification of characteristic features of monokaryons and of dikaryons formed therefrom The monokaryons obtained in step (A) or other monokaryons which are to form a new dikaryon are examined on different nutrient media for macroscopic, microscopic and biochemical features that are easy to identify and suitable for the characterization of a strain.

Table III

Characteristics suitable for characterizing monokaryons:

morphological charakteristics (a)

macroscopic features
growth rates on specific nutrient media
dense or loose mycelium
high or flat aerial mycelium
smooth, diffuse or lobed mycelium rim
formation of strands
feathery or wavy growth (b)

microscopic characteristics
short, swollen hyphal compartments
abundant, whorly branching to a varying degree
knobby hyphae
hyphae with pseudoclamp or clamp connections (c)

biochemical characteristics
require specific vitamins and nitrogen compounds
formation of dyes on specific nutrient media
formation of dyes after addition of specific chemicals
formation of characteristic crystals The monokaryons thus tested are mated with several well-known monokaryons and the resulting dikaryons are brought to fructification. They are tested as to whether a specific monokaryon inherits special properties which become visible only in the dikaryon, such as phototropic behavior of the fruit bodies, shape and color of the fruit bodies, wide or narrow spacing of the gills, abnormal spore number per basidium.

(E) Mating of selected monokaryons with new partners to form new dikaryons

Monokaryons which have shown desirable properties when mated with the testers in steps (C) and (D) are combined with selected partners to form new dikaryons. When selecting the partners attention is paid both to the properties which become manifest in the dikaryon, such as fructification at low light intensity, in specific temperature ranges, yield in fruit bodies and appearance, and to some characteristics which are easy to identify (see table III) and suitable for characterization of strains (see step G).

(F) Examination of the new dikaryons as to the stability of their characteristics by repeated dedikaryotization Before a dikaryon is tested on a larger scale on mushroom farms, the stability of its properties and of the properties of its components is tested and the strain is defined. The dikaryon is dedikaryotized according to the inventive process, the monokaryons thus obtained are examined for their characteristic features, subsequently combined in pairs to form dikaryons, which are also examined for their properties. If all essential characteristics have proved to be stable, then the old and some new dikaryons are again dedikaryotized according to the inventive process and the monokaryons obtained therefrom are compared with each other. If the monokaryons originating from the old and new dikaryons are identical with each other and with the initial strains, then the strain can be defined.

(G) Definition of the strains

Not only characteristic features of the dikaryon are stated, as has been customary hitherto. Rather, several characteristics of the monokaryons obtainable from the dikaryon by dedikaryotization are additionally indicated, these characteristics being easy to determine.

Example of a strain definition

Mushroom species, geographical race or climate type (or geographical race or climate type of the individual components of the dikaryon)
Cultivation and fruit body features of the dikaryon Characteristics of the monokaryon class 1 growth characteristics of the mycelium
special microscopic features
special biochemical features
special genes which become manifest in the dikaryon Characteristics of the monokaryon class 2 see under "characteristics of the monokaryon class 1" above

A dikaryon is unambiguously defined by the indication of at least 2 characteristics of the monokaryons obtainable by dedikaryotization and by the indication of the mating factors of these monokaryons; an unauthorized propagation can be unequivocally proven thereby. This follows from the mutation frequency of genes and from simple probability calculations. The mutation rate of fungi is from about $10^{-5}$ to $10^{-7}$ (see K. ESSER and R. RüHNEN, "Genetik der Pilze" (1967), Springerverlag, Berlin-Heidelberg-New York). As is known, mutagens can increase the frequency, in which a mutant occurs, by a factor of approximately 100. The probability for a dikaryon with 4 characteristics to occur again is the product of the individual probabilities and is consequently from about $10^{-20}$ ($10^{-5}\cdot 10^{-5}\cdot 10^{-5}\cdot 10^{-5}$) to $10^{-12}$ ($10^{-3}\cdot 10^{-3}\cdot 10^{-3}\cdot 10^{-3}$). In this calculation the mating factors are not yet taken into account. According to J. R. RAPER ("Genetics of Sexuality in higher Fungi", Ronald Press, New York 1966), the geographical distribution of the mating factors is a matter of chance. In the case of Pleurotus ostreatus with 63 A and 190 B factors, for example, (see under B), the probability of finding a specific A factor and a specific B factor a second time in nature is about 1:12 000. The mutability of mating factors is higher than the mutability of other genes and is about $10^{-3}$ (see also RAPER, loc. cit.) For a specific combination of a certain A factor with a certain B factor in the nuclei of a dikaryon the probability of recurrence is therefore at most about $10^{-2}$. Consequently, the probability for a specific dikaryon to recur decreases by an additional $10^{-4}$ if the mating factors are taken into consideration, and is thus from about $10^{-24}$ to $10^{-16}$. Such a dikaryon can therefore not be isolated from nature a second time, nor can it be produced from other strains with the aid of breeding techniques. The individual components of a dikaryon are sufficiently protected if the monokaryons obtained by dedikaryotizing this dikaryon are characterized by at least three features or genes. Considering its mating factors, the probability for such a monokaryon to recur is from about $10^{-18}$ to $10^{-11}$, that is to say its reproducibility (or repeatability) is likewise practically impossible. If the dedikaryotization of a strain distributed by an unauthorized spawn producer results in one or two monokaryons which are identical in all characterizing features and in the mating factors with monokaryons obtained by dekaryotizing a specific spawn, then the spawn producer has used one or both monokaryons from this specific spawn.

The examples illustrate the inventive process.

(A) Dedikaryotization of the initial material

Example 1

Dikaryons of, for instance, Pleurotus ostreatus, Pleurotus cornucopiae, Pleurotus eryngii, Flammulina velutipes, Kuehneromyces mutabilis, Lentinus edodes are used as initial material. In each case a deproteinated malt extract agar plate (see under step G) is inoculated with 1 to 3 inocula of the strain to be dedikaryotized and, depending on the mushroom species, incubated for 5 to 6 days at 24° to 28° C. The nutrient medium of a petri dish penetrated by the mycelium is treated in a sterile "semi-micro-container" of a "Waring-Blendor", which container is equipped with a cooling jacket, for 2.5 minutes at high speed (corresponding to 20,500 rpm* in empty state) with 50 ml of sterile, distilled water cooled down to 10° C. The final temperature in the container should not exceed 26° C. 20 μl of the container content are inoculated into 50 ml Erlenmayer flasks containing 25 ml of dedikaryotizing solution so that the mycelium fragment lie on the bottom of the liquid layer. The dedikaryotizing solution consists of 20 g glucose and 10 g "Peptone P" (by OXOID, L 49), dissolved in 1 liter of distilled water. It was sterilized for 15 minutes at 121° C. After incubation for 5 to 10 days at 24° to 28° C. (depending on the fungus strain and temperature), the mycelial fragments have grown in the liquid and developed into visible mycelial pellets. The flasks with the mycelial pellets and the flask with 30 ml portions of sterile, distilled water are now cooled down to 10° C. The mycelium from one flask, to which 30 ml water is added, is again fragmented under the same conditions as above in a sterile "semi-micro-container" of a "Waring Blendor", which container is equipped with a cooling jacket. 1 ml of the homogenate obtained is diluted with 15 ml sterile, distilled water and 10, 20 and 50 μl of the dilution are distributed on the surface of deproteinated malt extract agar plates. After 4 to 7 days of incubation at 24° to 28° C., depending on the mushroom species, the viable hyphal compartments have grown and form visible colonies which are almost exclusively monokaryons. The results are shown in table IV.

* revolutions per minute

Table IV

Dedikaryotization results after 5–10 days in a solution of 2% glucose and 1% "Peptone P" in distilled water

| mushroom species | dedikaryotization % | monokaryon classes per 20 colonies | |
|---|---|---|---|
| | | number | ratio |
| *Pleurotus ostreatus* | | | |
| commercial strain 1 | 100 | 2 | 3:2 |
| commmercial strain 2 | 98 | 2 | 2:1 |
| commercial strain 3 | 100 | 2 | 3:1 |
| commercial strain 4 (Florida type) | 100 | 2 | 5:4 |
| Strains: | | | |
| "42 × 11", sporeless | 100 | 2 | 3:2 |
| "V10", with low spore production | 100 | 2 | 3:2 |
| *Pleurotus cornucopiae* | | | |
| commercial strain | 80 | 2 | 5:4 |
| *Pleurotus eryngii* | | | |
| commercial strain | 100 | 2 | 3:1 |
| *Kuehneromyces mutabilis* | | | |
| Commercial strain | 100 | 2 | 3:1 |
| *Flammulina velutipes* | | | |
| commercial strain | 100 | 2 | 3:1 |
| *Lentinus edodes* | | | |
| commercial strain | 100 | 2 | 2:1 |

Example 2

The dikaryon "42×11" is inoculated into a deproteinated malt extract agar plate in petri dishes and incubated for 5 days at 28° C. The mycelium is dedikaryotized according to example 1, however, the dedikaryotizing solution consists of 20 g glucose and 3 g glycine diluted in 1 liter tap water with low degree of hardness (overall hardness 8 units on the German measurement scale, non-carbonate hardness 2.4; monophosphates 1.67 mg/liter. Table V shows the result of dedikaryotization.

Table V

Results of dedikaryotization in 10 days in a solution of 2% glucose and 0.3% glycine in tap water

| *Pleurotus ostreatus* | dedikaryotization % | monokaryon classes per 20 colonies | |
|---|---|---|---|
| | | number | ratio |
| strain "42 × 11", sporeless | 100% | 2 | 1:1 |

(B) Identification of the mating compatibility of monokaryons

Example 3

A pleurotus strain from Florida, which is also used commercially, serves as initial dikaryon. Individual spores, among them "42" and "11" were isolated from a fruit body. After mating, they form a sporeless dikaryon. This dikaryon is dedikaryotized according to example 1 or 2. Two morphologically different classes of monokaryons result:

Class 1: slow-growing colonies with high aerial mycelium (corresponds to monokaryon "11")
Class 2: faster-growing colonies with flat aerial mycelium (corresponds to monokaryon "42")

Both monokaryon classes are mated with 4 testers for the mating factors (MF) of the initial dikaryon. Among these, tester 1 is compatible with tester 2 and tester 3 with tester 4. The results are shown in table VI.

Table VI

Result of mating the monokaryons (Nh) originating from the dikaryon "42 × 11" with the testers for the MF of Pleurotus from Florida

| Nh Class | | Tester 1 | Tester 2 | Tester 3 | Tester 4 | Classification of the Nh |
|---|---|---|---|---|---|---|
| 1, corresponds to "11" | 1 | − | + | − | − | |
| | 2 | − | + | − | − | they correspond to tester 1 |
| | 3 | − | + | − | − | |
| | 4 | − | + | − | − | |
| | 5 | − | + | − | − | |
| 2, corresponds to "42" | 1 | + | − | − | − | |
| | 2 | + | − | − | − | they correspond to tester 2 |
| | 3 | + | − | − | − | |
| | 4 | + | − | − | − | |
| | 5 | + | − | − | − | |

Accordingly, within the individual classes the monokaryons also coincide in their mating factors.

Example 4

A subculture of the Pleurotus dikaryon of example 3, which was further subcultivated several times within 5 years in a different place, was used to produce fruit bodies and, by isolating individual spores, monokaryons were prepared. The monokaryon "J136" was paired with the testers for the mating factors (MF) of the Pleurotus from Florida. Of these, tester 1 and tester 2 and testers 3 and 4 are compatible with each other. The results are shown in table VII.

Table VII

Result of mating the monokaryon "J136" with testers for MF of Pleurotus from Florida

| | Tester 1 | Tester 2 | Tester 3 | Tester 4 | Classification of the MF of the monokaryon |
|---|---|---|---|---|---|
| "J136" | − | − | − | + | they correspond to tester 3 |

Since "J136" is compatible only with tester 4, it has the same mating factors as tester 3.

(C) Identification of the genes for sporelessness, in monokaryons

Example 5

Monokaryon "J136" and other monokaryons of the same origin are mated with a compatible tester for sporelessness, for example "12a". The results are shown in table VIII. Accordingly, only "J136" contains a gene for sporelessness.

Table VIII

Proof of genes for sporelessness by mating with a tester for sporelessness

| Monokaryon | × | Tester | 12a | Result of the matings |
|---|---|---|---|---|
| J 136 | × | Tester | 12a | sporeless fruit body |
| J 88 | × | Tester | 12a | fruit body with many spores |
| J 105 | × | Tester | 12a | fruit body with many spores |
| J 109 | × | Tester | 12a | fruit body with many spores |
| J 161 | × | Tester | 12a | fruit body with many spores |
| J 202 | × | Tester | 12a | fruit body with many spores |

Example 6

Dikaryon "V10" shows low spore production, i.e. the fruit bodies have on each gill sporadic spores. This dikaryon was produced from a *Pleurotus ostreatus* strain from Michigan by treating the strain with N-methyl-N'-nitro-N-nitrosoguanidine. Dedikaryotized according to example 1, "V10" gives two classes of monokaryons, which can be distinguished microscopically (see example 7).

Class 1 has the monokaryons 1,2,3,6,8
Class 2 has the monokaryons 4,5,7,9,10

The monokaryons are paired with a tester for sporelessness, for example "M17". The results are shown in table IX.

Table IX

| Monokaryons | = | Tester | Result of matings |
|---|---|---|---|
| 1,2,3,6,8 | = | M17 | 5 dikaryons with sporeless fruit bodies |
| 4,5,7,9,10 | = | M17 | 5 dikaryons, fruit bodies with a large number of spores |

Accordingly, the monokaryons 1,2,3,6 and 8 contain genes for sporelessness.

(D) Identification of characteristic features of monokaryons and of dikaryons formed therefrom

Example 7

According to example 6, the dikaryon "V10" forms two classes of monokaryons. The monokaryons of class 1 grow slowly. They have a smooth margin and high aerial mycelium on deproteinated malt extract (see below step G). The monokaryon "nh2" was thoroughly tested. The growth rates on deproteinated malt agar and on potato-dextrose agar are identical. If three drops of Guajacol (Merck 4212) are placed at room temperature with a Pasteur pipette on one spot near the margin of a six-day old mycelium grown in the dark on deproteinated malt extract agar at 24° to 28° C., a characteristic color reaction takes place. An apricot-colored halo forms around the Guajacol within 20 minutes, which becomes rust-colored within a further 40 minutes and finally turns chestnut-brown (after 2 or more hours). With 4 drops of a 1% solution of α-naphthol in 50% ethanol, the same mycelium produces a dark livid (lead-colored) violaceous staining of the agar within 60 minutes, which can be observed especially well on the underside of the culture. Several drops of a 1% solution of p-anisidin in 20% ethanol placed directly on the agar beside the mycelium produce a dark vinaceous staining of the agar after 30 to 60 minutes. Monokaryons of class 2 grow extremely slowly. The monokaryon "nh4" was examined under the microscope. It has clamp connections. With monokaryons or different origin (not from dikaryon "V10"), which have proved to carry genes for sporelessness, it either forms no fruit bodies or fruit bodies which show low spore production. About 50% of the basidia of fruit bodies with low spore production are 5 or 6-spored.

(E) Mating of selected monokaryons with new partners to form new dikaryons

Example 8

The slow growing monokaryon "nh2" of example 7 is paired with monokaryon "M17" (tester). The new dikaryon has a growth rate which is comparable to that of successful commercial strains. It is sporeless.

(F) Examination of the new dikaryons as to the stability of their characteristics by repeated dedikaryotization

Example 9

The dikaryon "42×11" and the monokaryon (Nh) "42" and "11" obtainable therefrom according to example 1 or 2 possess the characteristics listed in example 12. These were tested as to stability by repeated dedikaryotization in the following way:

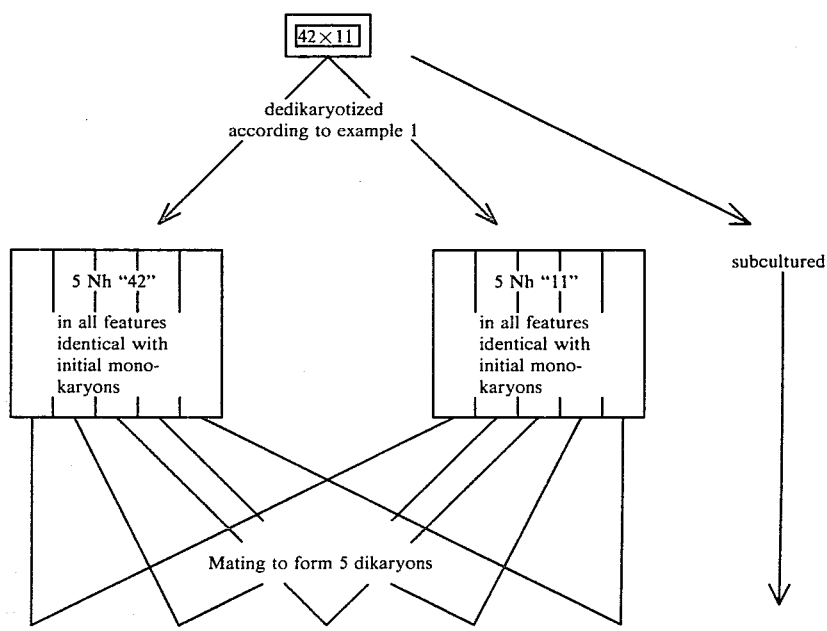

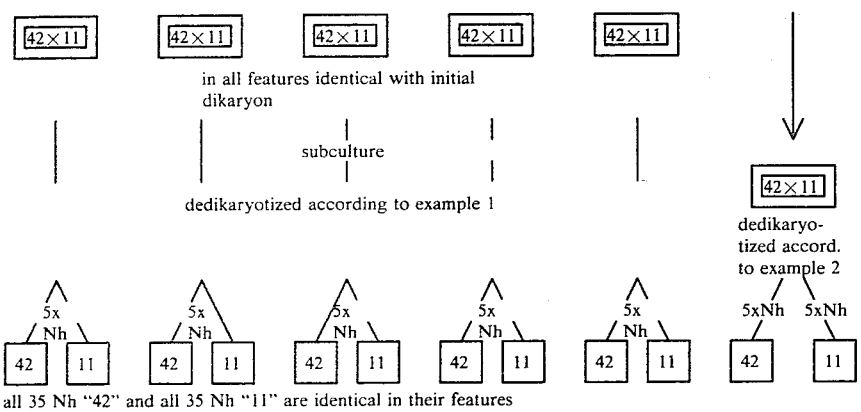

all 35 Nh "42" and all 35 Nh "11" are identical in their features (G) Definition of the strains The following examples contain symbols for specific nutrient media, namely:

DPMA = deproteinated malt extract agar 20 g "Maltzin ® trocken, hell" by DIAMALT (Munich) are dissolved in 250 ml of distilled water. The pH value of the solution is increased by 1.5 by titration with 1 n NaOH. Then 1.4 $CaCl_2.2H_2O$ are added, mixed and autoclaved for 15 minutes at 121° C. After cooling to room temperature the mixture is filtered. 75 ml of the filtrate, 425 ml distilled water and 7.6 g agar (MERCK 1614) are mixed and sterilized for 15 minutes at 121° C. The agar plates contain 15 ml of said medium in petri dishes having a diameter of 8.5 cm.

GPPA = Glucose-Peptone P agar 10 g D-Glucose-Monohydrate (MERCK 8342) for biochemical purposes, 5 g Peptone P (OXOID, L 49), 7.6 agar (MERCK 1614), 500 ml distilled water are mixed and sterilized for 15 minutes at 121° C. Agar plates as above.

PDA = Bacto-Dehydrated Potato Dextrose Agar (DIFCO) as stated on the pack. Agar plate as above.

The color reactions are carried out with 6 day-old mycelia grown on DPMA at 24° to 28° C. in the dark. The following reagents are used:

Guajacol (MERCK 4212)
α-naphthol: 1% solution in 50% ethanol
p-anisidin: 1% solution in 20% ethanol Guajacol and α-naphthol are placed on the mycelium near the margin (3-4 drops), the p-anisidin is placed on the agar next to the mycelium. The colors are denominated in accordance with "A Mycological Colour Chart" by R. W. RAYNER (1970), published by "Commonwealth Mycological Institute Kew", Surrey, and "British Mycological Society". Color numbers followed by the name are indicated.

Example 10

Dikaryon "V10"

*Pleurotus ostreatus* from Michigan, U.S.A., corresponds to *Pleurotus sapidus* of some North-American authors.

Grows slower than commercial strains. Fructification from +5° to 27° C. Fruit bodies show low spore production. Up to 50% of the basidia have more than 4 (5 or 6) spores.

Features of monokaryon class 1 (corresponding to "nh2" of example 7)

1. on DPMA, mycelium with smooth margin
2. on DPMA, high conic aerial mycelium
3. growth rates on DPMA and PDA approximately the same
4. p-anisidin reaction: color change within 30 to 60 minutes to 56 (livid red) and to 82 (dark wine red)
5. gene(s) for sporelessness Features of monokaryon class 2 (corresponding to "nh4" of example 7)

1. hyphae with clamp connections
2. when mated with tester for sporelessness (see examples 5 and 6) dikaryons are obtained which give fruit bodies with low spore production
3. gene(s) for high content (50%) of 5 and 6-spored basidia.

This definition of strain "V10" contains only part of the characteristics of the monokaryon stated in example 7. Some of the features are hardly specific, such as the Guajacol and the α-naphthol reaction (they can be observed with many strains) or they can be easily removed by breeding, such as extremely slow growth.

Example 11

Dikaryon "nh2×M17"

*Pleurotus ostreatus* from Michigan, U.S.A., corresponds to *Pleurotus sapidus* of some North American authors.

Growth rate corresponds to that of commercial strains. Fructification from +5° to 27° C. Fruit bodies sporeless.

Features of monokaryon class "nh2"

See example 10.

Features of monokaryon class "M17"

1. no or very weak reaction with Guajacol
2. no or very weak reaction with α-naphthol
3. no or very weak reaction with p-anisidin
4. when mated with testers for sporelessness, dikaryons are produced which give fruit bodies with no spore production.

Example 12

Dikaryon "42×11"

*Pleurotus ostreatus* from Florida, U.S.A.

Fast growing mycelium, fructification extremely slow at temperatures below 10° C., good at 20° to 30° C. Fruit bodies sporeless, radially symmetric as a result of an abnormal, phototropic reaction.

Features of monokaryon class "42"

1. growth of approximately 50 mm (mycelium diameter) on DPMA at 24° C. in the dark in 6 days (inoculum 2 mm)
2. mycelium margin smooth
3. no or very weak reaction with Guajacol
4. no or very weak reaction with α-naphthol
5. no or very weak reaction with p-anisidin
6. gene(s) for sporelessness Features of monokaryon class "11"

1. on DPMA, mycelium with diffuse margin
2. on DPMA, high conic aerial mycelium
3. growth rates on DPMA and PDA are the same
4. color-change with p-anisidin to 59 (brick-red) in 30 to 60 minutes.
5. when mated with tester for sporelessness, dikaryons are obtained with give sporeless fruit bodies.

Example 13

Dikaryon "J136×12a"

*Pleurotus ostreatus* from Florida, USA.

Fast growing mycelium, fructification extremely slow at temperatures below 10° C., good at 20° to 30° C. Sporeless fruit bodies.

Features of monokaryon class "J136"

1. on DPMA and PDA, mycelium more or less lobed
2. on GPPA growth after 7 to 14 days at 24° C. in the dark, change in color starting from the inoculum to 11 (pale yellow), 12 (yellow), 39 (rust) and finally to 9 (umber)*
3. genes for sporelessness

*reddish-brown

Features of monokaryon class "12a"

1. on DPMA and PDA, mycelium more or less lobed
2. growth rate on GPPA at 24° C. in the dark insubstantially lower (about 10%) than on PDA
3. on GPPA growth after 7 to 14 days at 24° C. in the dark, change in color starting from the inoculum to 11 (pale yellow), 12 (yellow), 8 (sienna) and finally to 39 (rust)
4. when mated with tester for sporelessness, produces dikaryons which give sporeless fruit bodies.

Deposition of the Strains

All strains defined herein are deposited as patent strains at the Northern Research Laboratory of the U.S. Department of Agriculture, 1815 North University St., Peoria, Ill. 61604 U.S.A. and have been assigned the following deposition numbers:

| 42 | NRRL 11 241 | nh4 | NRRL 11 247 |
|---|---|---|---|
| 11 | NRRL 11 242 | 12a | NRRL 11 248 |
| 42 × 11 | NRRL 11 243 | J136 | NRRL 11 249 |
| M17 | NRRL 11 245 | V10 | NRRL 11 250 |
| nh2 | NRRL 11 246 | J136 × 12a | NRRL 11 251 |
|  |  | nh2 × M17 | NRRL 11 252 |

Commercial strains of Pleurotus species, Kuehneromyces, Flammulina and Lentinus have not been deposited. They can either be obtained from spawn producers or easily isolated from marketed fruit bodies via so-called "tissue cultures".

We claim:

1. A process for preparing a monokaryon by dedikaryotizing a dikaryotic strain of Basidiomycetes comprising the following steps: (a) mechanically fragmenting the mycelium of a dikaryotic strain of Basidiomycetes in an aqueous medium to give viable mycelial fragments having predominantly one to a very few hyphal compartments, (b) introducing a small potion of the mycelial fragments so obtained into a dedikaryotizing solution containing glycine and at least one carbon source, (c) incubating the fragments, while keeping them covered by at least 2 mm of said dedikaryotizing solution, to allow the fragments to grow into spatially isolated mycelial pellets, (d) inspecting random samples of said mycelial pellets to determine the degree of dedikaryotization, (e) fragmenting visible mycelial pellets in an aqueous medium to give hyphal fragments having one or a very few cells, (f) placing the resulting hyphal fragments on or in a nutrient agar plate and allowing said fragments to grow into spatially isolated individual monokaryotic colonies, and (g) transferring at least one of said monokaryotic colonies to new nutrient medium.

2. A process according to claim 1, wherein said dedikaryotizing solution contains at least one carbon source as well as a neutral meat peptone having a high glycine content and a low phosphate and magnesium ion content.

3. Process according to claim 2, characterized in that the meat peptone is "Peptone P" (by Dxoid, L49).

4. Process according to claim 2, characterized in that the dedikaryotizing solution contains 0.02 to 7% meat peptone.

5. Process according to claim 2, characterized in that the dedikaryotizing solution contains a mixed peptone containing "Peptone P" or at least the other neutral meat peptone.

6. Process according to claim 1, characterized in that the dedikaryotizing solution contains 0.01 to 5% glycine.

7. Process according to claim 1, characterized in that the dedikaryotizing solution is supplemented with vitamins and/or nitrogen-containing compounds.

8. Process according to claim 1 or 2, characterized in that the mycelium of Basidiomycetes dikaryons which produce few or no spores is used.

9. Process according to claim 1 or 2, characterized in that mycelium of the genus Pleurotus is used.

10. Process according to claim 9, characterized in that mycelium of *Pleurotus ostreatus* is used.

11. Process according to claim 1 or 2, characterized in that mycelium of *Kuehneromyces mutabilis* is used.

12. Process according to claim 1 or 2, characterized in that mycelium of *Flammulina velutipes* is used.

13. Process according to claim 1 or 2, characterized in that mycelium of Shiitake (*Lentinus ebodes*) is used.

14. A process wherein two compatible monokaryons produced according to the process of claim 1 are mated to form a dikaryotic Basidiomycetes strain.

15. A process wherein two compatible monokaryons produced according to the process of claim 2 are mated to form a dikaryotic Basidiomycetes strain.

* * * * *

UNITED STATES PATENT AND TRADEMARK OFFICE
CERTIFICATE OF CORRECTION

PATENT NO. : 4,242,832
DATED : January 6, 1981
INVENTOR(S) : Gerlind Eger et al.

It is certified that error appears in the above—identified patent and that said Letters Patent is hereby corrected as shown below:

Column 6, line 27, "charakteristics" should read -- characteristics --.

Column 9, line 40, after "liter" insert -- ) --.

Column 11, In Table IX, change all " = " to -- X --.

Column 12, line 16, "or" should read -- of --.

Column 16, line 60, "ebodes" should read -- edodes --.

Signed and Sealed this

Twenty-third Day of June 1981

[SEAL]

Attest:

RENE D. TEGTMEYER

Attesting Officer          Acting Commissioner of Patents and Trademarks